(12) United States Patent
Hong et al.

(10) Patent No.: US 9,540,319 B2
(45) Date of Patent: Jan. 10, 2017

(54) METHOD FOR PURIFYING SULFONATED AROMATIC MONOMER

(75) Inventors: Young Taik Hong, Daejeon (KR); Seog Je Kim, Daejeon (KR); Ji Young Park, Gyeongsangnam-do (KR); Dong Hyun Lee, Daejeon (KR)

(73) Assignee: KOREA RESEARCH INSTITUTE OF CHEMICAL TECHNOLOGY (KR)

( * ) Notice: Subject to any disclaimer, the term of this patent is extended or adjusted under 35 U.S.C. 154(b) by 239 days.

(21) Appl. No.: 13/825,692

(22) PCT Filed: Nov. 14, 2011

(86) PCT No.: PCT/KR2011/008668
§ 371 (c)(1),
(2), (4) Date: Mar. 22, 2013

(87) PCT Pub. No.: WO2012/070793
PCT Pub. Date: May 31, 2012

(65) Prior Publication Data
US 2014/0206899 A1    Jul. 24, 2014

(30) Foreign Application Priority Data
Nov. 26, 2010    (KR) .................. 10-2010-0118599

(51) Int. Cl.
*C07C 309/01* (2006.01)
*C07C 315/06* (2006.01)

(52) U.S. Cl.
CPC .................. *C07C 315/06* (2013.01)

(58) Field of Classification Search
CPC .................................. C07C 303/32
USPC ..................................... 562/75, 83
See application file for complete search history.

(56) References Cited

U.S. PATENT DOCUMENTS 2,847,459 A * 8/1958 Mitchell .................... 562/95
4,239,885 A * 12/1980 Richmond ........... C07D 265/10
                                                        544/97
5,438,082 A    8/1995 Helmer-Metzmann et al.
6,183,648 B1 * 2/2001 Kozak .................. B01D 61/027
                                                        210/650
6,245,881 B1    6/2001 Faure et al.

FOREIGN PATENT DOCUMENTS

JP    06093114    4/1994

OTHER PUBLICATIONS

Harrison, Journal of Polymer Science, Part A: polymer chemistry, 2003, 41, 2264-2276.*
Li, Xianfeng et al.,"Direct synthesis of sulfonated poly(ether ether ketone ketone)s (SPEEKKs) proton exchange membranes for fuel cell application" Polymer vol. 46 (2005) 5820-5827.
Li, Yanxiang et al., "Purity characterization of 3,30-disulfonated-4,40-dichlorodiphenyl sulfone (SDCDPS) monomer by UV—vis spectroscopy" Polymer vol. 49 (2008) 3014-3019.
Sankir, et al., "Synthesis and Characterization of 3,3'-Disulfonated-4,4'-dichlorodiphenyl Sulfone (SDCDPS) Monomer for Proton Exchange Membranes (PEM) in Fuel Cell Applications" J. Appl. Polym. Sci. 2006, 100, 4595-4602.
Einsla, Brian et al., "Direct copolymerization of wholly aromatic and partially fluorinated disulfonated poly(arylene ether sulfone)s" Preprint Symp. Acs, Div. Fuel Chem. 2005, vol. 50, 571-572.
Nolte et al., Partially sulfonated poly (arylene ether sulfone)—A versatile proton conducting membrane material for modern energy conversion technologies, Journal of Membrane Science, 83, 1993, 211-220, Elsevier Science Publishers B.V., Amsterdam.
Harrison et al., Influence of the Bisphenol Structure on the Direct Synthesis of Sulfonated Poly(arylene ether) Copolymers, Journal of Polymer Science, Part A: polymer chemistry, 2003, 41, 2264-2276.

* cited by examiner

*Primary Examiner* — Sudhakar Katakam
*Assistant Examiner* — Sonya Wright
(74) *Attorney, Agent, or Firm* — Levenfeld Pearlstein, LLC

(57) ABSTRACT

The present invention relates to an improved method for purifying a sulfonated aromatic monomer. The method is an economical method capable of providing a highly pure sulfonated aromatic monomer, in which a salt precipitation step and a recrystallization step are simplified while maintaining the reaction conditions used in a conventional method for synthesizing the sulfonated aromatic monomer, and a purification process is carried out using an easily available and stable chemical substance. The sulfonated aromatic monomer obtained by the purification method will be useful for the preparation of a polymer for a polymer electrolyte membrane and will be advantageous to synthesize polymer with high molecular weight.

3 Claims, 4 Drawing Sheets

METHOD FOR PURIFYING SULFONATED AROMATIC MONOMER

CROSS-REFERENCE TO RELATED APPLICATIONS

This is a National Stage Application of International Patent Application No. PCT/KR2011/008668, filed Nov. 14, 2011, which claims the benefit of and priority to Korean Patent Application No. 10-2010-0118599, filed Nov. 26, 2010, the contents of each of which are incorporated fully by reference herein.

TECHNICAL FIELD

The present invention relates to an improved method for purifying a sulfonated aromatic monomer, and more particularly to an economical method for purifying a sulfonated aromatic monomer, in which a salt precipitation step and a recrystallization step are simplified while maintaining the reaction conditions used in a conventional method for synthesizing the sulfonated aromatic monomer, and a purification process is carried out using an easily available and easy-to-handle chemical substance.

BACKGROUND ART

Fuel cells are generally classified, according to operating temperature and electrolyte, into an alkaline fuel cell (AFC), a phosphoric acid fuel cell (PAFC), a molten carbonate fuel cell (MCFC), a solid oxide fuel cell (SOFC), a polymer electrolyte membrane fuel cell (PEMFC) and a direct methanol fuel cell (DMFC). Among them, the polymer electrolyte membrane fuel cell and the direct methanol fuel cell, which have excellent mobility, are receiving a great deal of attention as power sources.

Generally, a solid polymer fuel cell comprises a gas diffusion electrode layer disposed on both sides of a polymer electrolyte membrane, an anode as a negative electrode (reduction), and a cathode as a positive electrode (oxidation). In this fuel cell, water is produced by a chemical reaction in the polymer electrolyte membrane, and energy produced by this reaction is converted into electrical energy.

However, in the solid polymer electrolyte fuel cell, hydrogen peroxide ($H_2O_2$) is produced as a result of side reactions during the reduction of oxygen in the cathode. Hydrogen peroxide or peroxide radicals, produced in the cathode electrode layer, can deteriorate the electrolyte of the cathode electrode layer or the polymer electrolyte membrane adjacent thereto. In addition, if a phenomenon (crossover) occurs in which oxygen molecules pass from the cathode through the polymer electrolyte membrane to the opposite electrode, hydrogen peroxide or peroxide radicals will also be produced in the anode, potentially resulting in deterioration of the electrolyte of the anode electrode layer.

Ion conductive polymer electrolyte membranes developed in view of such problems are mostly perfluorinated polymer electrolyte membranes and are commercially available as Nafion (DuPont, USA), Aciplex-S membrane (Asahi Chemicals), Dow membrane (Dow Chemicals), Flemion membrane (Asahi Glass), etc.

Commercially available perfluorinated polymer electrolyte membranes have chemical resistance, oxidation resistance and excellent ion conductivity, but are costly and pose environmental problems due to the toxicity of intermediate products generated during the production thereof.

In order to overcome such drawbacks of the perfluorinated polymer electrolyte membranes, polymer electrolyte membranes comprising a carboxyl group, a sulfonic acid group or the like introduced into an aromatic ring polymer have been studied. Examples of such perfluorinated polymer electrolyte membranes include sulfonated polyarylether sulfone (*Journal of Membrane Science*, 1993, 83, 211), sulfonated polyetherether ketone (Japanese Patent Laid-Open Publication No. Hei 6-93114, and U.S. Pat. No. 5,438,082), and sulfonated polyimide (U.S. Pat. No. 6,245,881).

Accordingly, the present invention discloses a sulfonated aromatic monomer for preparing the above-described polymer introduced with a sulfonic acid group.

Generally, the sulfonated aromatic monomer is prepared according to the following reaction scheme 1. Specifically, as shown in reaction scheme 1, a target compound 1 is prepared by allowing an aromatic monomer 3 to react with fuming sulfuric acid to obtain a sulfonated compound 2 and adding a salt (NaCl) thereto.

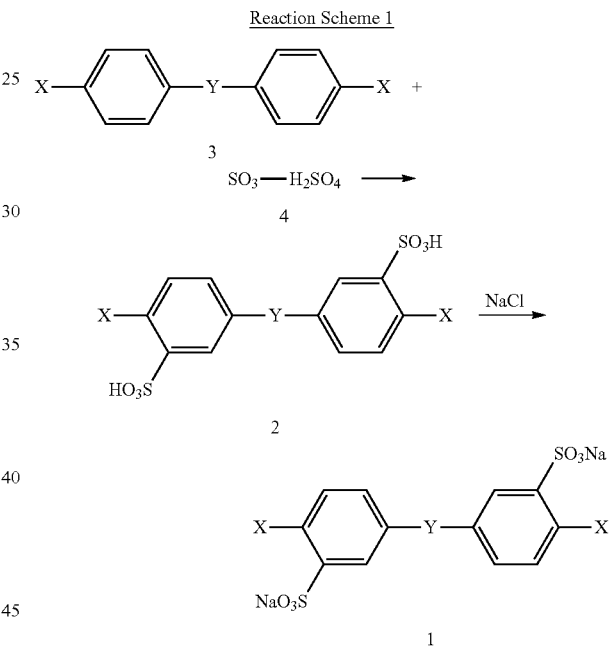

Reaction Scheme 1 wherein X is a halogen group element, and Y is any one selected from the group consisting of —S—, —C=O—, —P(O)(C$_6$H$_5$)— and —SO$_2$—.

However, as shown in FIG. 1 showing a conventional process for purifying a sulfonated aromatic monomer, many process steps are used to obtain the target compound with high purity, and thus the conventional process is disadvantageous in terms of yield and cost.

More specifically, the sulfonated aromatic monomer is to provided by a known method (*Journal of polymer science: Part A: polymer chemistry*, 2003, 41, 2264-2276). In the known method, a salt precipitation step is carried out twice, resulting in a decrease in yield. Also, because a strong base (NaOH) is used in a neutralization process, a change in the pH of the reaction product occurs even when the amount of the base slightly changes, and thus it is not easy to control the pH. In addition, the use of the strong base (NaOH) causes side reactions. Moreover, a recrystallization process is carried out in a 50:50 (v/v) mixture of alcohol and water. Because the desired compound dissolves in water, but does not easily dissolve in alcohol, it does not easily dissolve in the water/alcohol mixture, and thus the mixture can be used as a recrystallization solvent. However, for recrystallization, the water/alcohol mixture should be used in an amount corresponding to about 30-40 times that of the target compound 1. Thus, the loss of the solvent will result, and the salt (NaCl) can be recrystallized due to the use of excessive amount of the solvent.

Accordingly, the present inventors have made extensive efforts to overcome the problems of the conventional process for preparing the sulfonated aromatic monomer, have found a method for synthesizing a highly pure sulfonated aromatic monomer, which comprise a reduced number of salt precipitation steps, a simplified recrystallization process, and a purification process which is carried out using an easily available and stable chemical substance under mild conditions, thereby completing the present invention.

DISCLOSURE

Technical Problem

It is an object of the present invention to provide an improved method for purifying a sulfonated aromatic monomer. More specifically, an object of the present invention is to provide an economical method for preparing a sulfonated aromatic monomer, in which a salt precipitation step and a recrystallization step are simplified while maintaining the reaction conditions used in a conventional process for preparing the sulfonated aromatic monomer.

Technical Solution

In order to accomplish the above object, the present invention provides a method for purifying a sulfonated aromatic monomer 1 as shown in the following reaction scheme 2, the method comprising the steps of: allowing an aromatic monomer 3 to react with fuming sulfuric acid 4 to prepare a sulfonated aromatic compound 2; adding a salt to the compound 2 to precipitate a crude compound 1-1; dissolving the crude compound 1-1 in water; neutralizing the aqueous solution containing the crude compound; and concentrating the neutralized aqueous solution and recrystallizing the concentrate from water:

In the purification method of the present invention, the salt precipitation step is carried out by adding the salt to the compound 2 placed on ice.

In addition, the dissolution step in the purification method of the present invention is carried out after washing with any one alcohol selected from among methanol, ethanol or a mixture thereof.

In the neutralization step in the method of the present invention is carried out using a solution containing any one weak base selected from among sodium carbonate, sodium hydrogen carbonate, ammonium hydroxide, ammonia, sodium phosphate, and sodium sulfate.

The neutralization step in the method of the present invention may be carried out by neutralizing the aqueous solution with anion exchange resin, followed by a washing step. When the neutralization step using anion exchange resin is carried out, the method of the present invention may further comprise, after the neutralization step, a step of washing the used anion exchange resin with a base to removing a compound attached to the anion exchange resin. Herein, the base is used in the same amount as the anion exchange resin.

Advantageous Effects

As described above, the present invention can provide an improved method for purifying a sulfonated aromatic monomer.

In the improved purification method of the present invention, a salt precipitation step and a recrystallization step are simplified while maintaining the reaction conditions used in a conventional method for preparing the sulfonated aromatic monomer, and the purification process is carried out using an easily available and easy-to-handle chemical substance under economical and mild conditions. According to this method of the present invention, a highly pure sulfonated aromatic monomer can be obtained.

Reaction Scheme 2

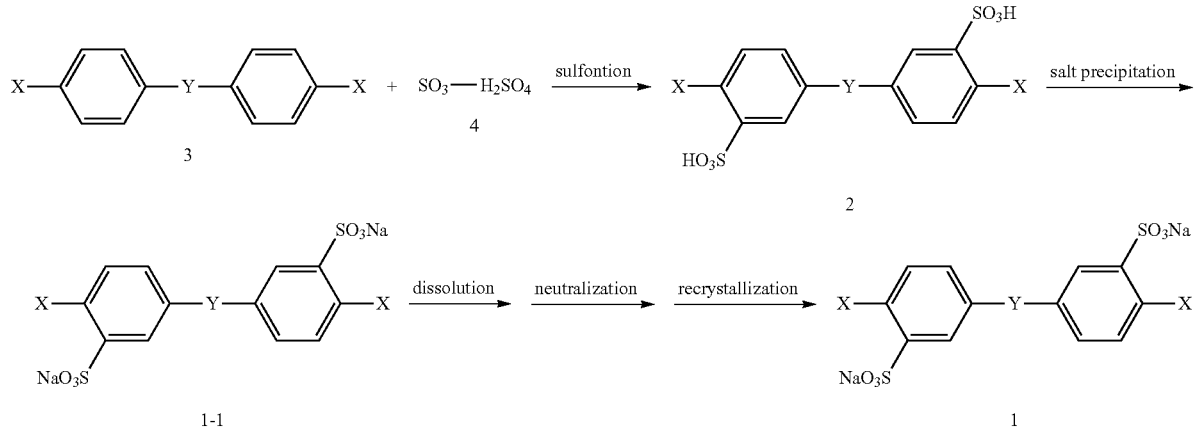

Figure 3:
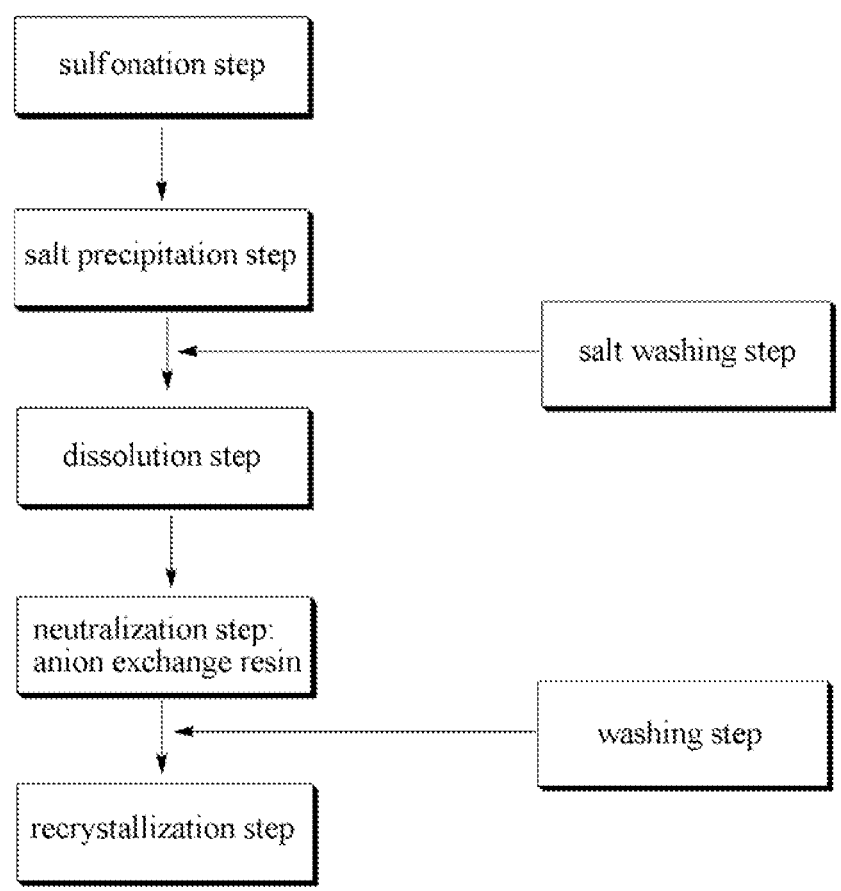
Figure 4:
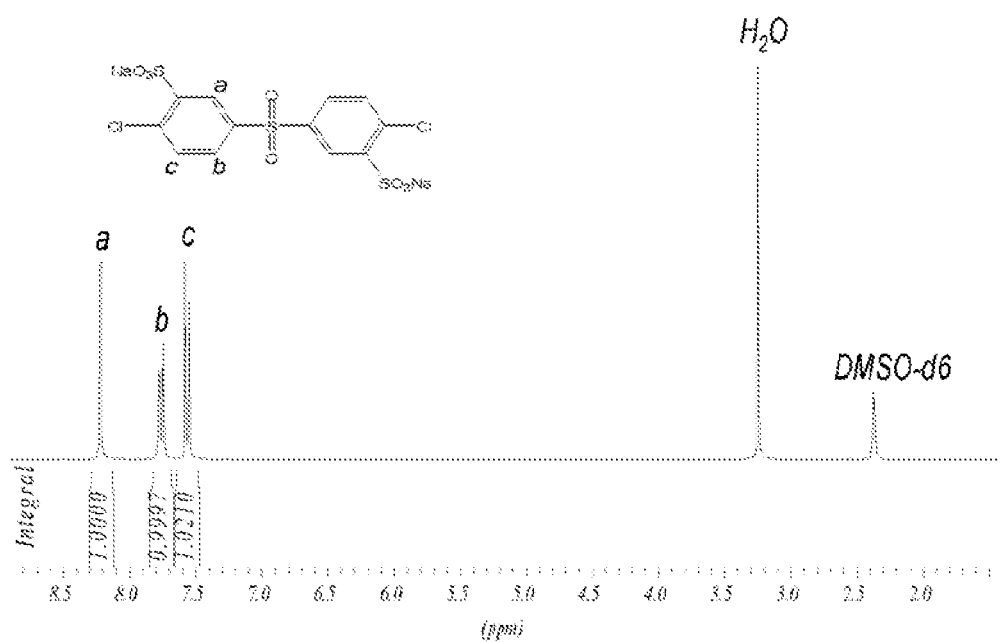

FIG. 3 is a flowchart showing a process for purifying a sulfonated aromatic monomer according to a second preferred embodiment of the present invention; and FIG. 4 shows the $^1$H NMR spectrum of the sulfonated aromatic monomer purified according to the first and second embodiments of the present invention.

BEST MODE

Hereinafter, the present invention will be described in further detail.

The present invention provides a method for purifying a sulfonated aromatic monomer 1 as shown in the following reaction scheme 2, the method comprising the steps of: allowing an aromatic monomer 3 to react with fuming sulfuric acid 4 to prepare a sulfonated aromatic compound 2; adding a salt to the compound 2 to precipitate a crude compound 1-1; dissolving the crude compound 1-1 in water; neutralizing the aqueous solution containing the crude compound; and concentrating the neutralized aqueous solution and recrystallizing the concentrate from water:

The dissolution step in the purification method of the present invention is a step of dissolving the crude compound 1-1 in water, like that of the conventional method. However, the dissolution step of the present invention is characterized in that the crude compound 1-1 is dissolved in water after washing with alcohol. Herein, the alcohol that is used in the dissolution step is preferably methanol, ethanol or a mixture thereof. More preferably, the alcohol is any one selected from among methanol and ethanol.

When the crude compound 1-1 is washed with alcohol, a sulfuric acid component remaining in the crude compound 1-1 can be removed by washing, and thus the purity of the target compound can be increased.

Next, the neutralization step is carried out. In a preferred embodiment of the present invention, the neutralization step is carried out using a weak base. More preferably, it is carried out using any one weak base selected from the group consisting of sodium carbonate, sodium hydrogen carbonate, ammonium hydroxide, ammonia, sodium phosphate, and sodium sulfate.

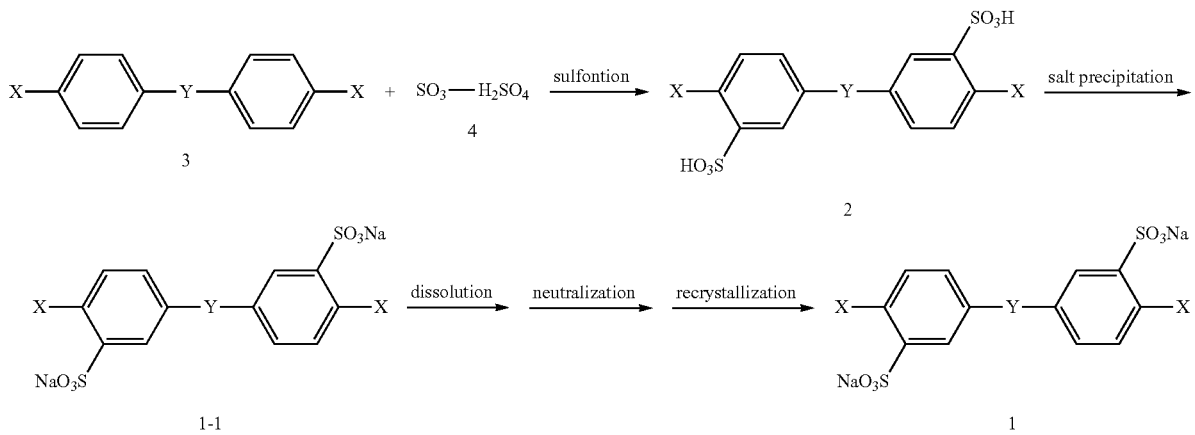

Reaction Scheme 2 wherein X is a halogen group element, and Y is any one selected from the group consisting of —S—, —C=O—, —P(O) (C$_6$H$_5$)— and —SO$_2$—.

The improved method for purifying the sulfonated aromatic monomer 1 according to the present invention is characterized in that the salt precipitation step and the recrystallization step are simplified while maintaining the reaction conditions used in a conventional method for purifying the sulfonated aromatic monomer.

Specifically, the steps of obtaining the sulfonated aromatic compound 2 by sulfonation and adding the salt (NaCl) to the sulfonated aromatic compound 2 to obtain the compound 1-1 are the same as those of the conventional method.

However, in the salt precipitation step of the conventional process, the sulfonated aromatic compound 2 obtained by reacting the aromatic monomer with 20-60%; fuming sulfuric acid for 4-12 hours is added to the salt (NaCl) in an ice/waster (50%) solution to precipitate the compound (1-1).

In comparison with this, in the purification of the present invention, the sulfonated aromatic compound 2 is added to the salt (NaCl) on ice alone and stirred to obtain the compound 1-1.

When the sulfonated aromatic compound 2 is added to ice to precipitate the salt, the generation of heat can be prevented, and thus a reaction time of 6 hours or longer in the conventional method can be shortened to 1 hour or shorter in the method of the present invention.

Sodium carbonate (NaCO$_3$) is used in the neutralization step in the most preferred embodiment of the present invention, but any conventional weak base may be used without limitation in the present invention, as long as it can neutralize the compound to a pH of 6-7. Also, in the neutralization step of the present invention, if the range of the pH to be adjusted is broad, the pH may be first adjusted with 10% NaOH solution, and then adjusted with a weak base solution.

Thus, according to the present invention, the neutralization step can be easily performed without causing a change in pH that result from the use of a strong base (NaOH) in the conventional method.

In another embodiment of the present invention, the neutralization step is carried out using anion exchange resin. Specifically, the crude compound 1-1 dissolved in water in the dissolution step is neutralized by passage through anion exchange resin. The neutralization step employing anion exchange resin may be repeated 1-3 times.

When the anion exchange resin is used, a large amount of NaCl dissolved in the aqueous solution of the crude compound 1-1 can be removed by washing. After the neutralization step employing the anion exchange resin, washing with a base is carried out to detach the compound 1-1 attached to the anion exchange resin, and the detached compound 1-1 is neutralized in the next neutralization step. Herein, the base is used in the same amount as the anion exchange resin.

The recrystallization step in the purification method of the present invention is carried out by concentrating the aqueous solution resulting from the neutralization step and recrystallizing the concentrate from water.

However, the recrystallization step in the conventional purification method is carried out in a mixed solvent of alcohol and water (50:50 v/v). Because the compound 1-1 does not easily dissolve in the mixed solvent of water and alcohol, the alcohol/water mixture should be used in an amount corresponding to 30-40 times that of the compound 1 in order to recrystallize the compound 1. In comparison with this, in the method of the present invention, a crystal can be recovered by removing a slight amount of water from the aqueous solution, and thus the recrystallization step can be simplified compared to the conventional method.

In addition, the method of the present invention can eliminate the problem of the conventional method in which an excessive amount of the solvent is used to increase the purification cost or the salt (NaCl) is recrystallized in an excessive amount of the solvent.

Figure 1:
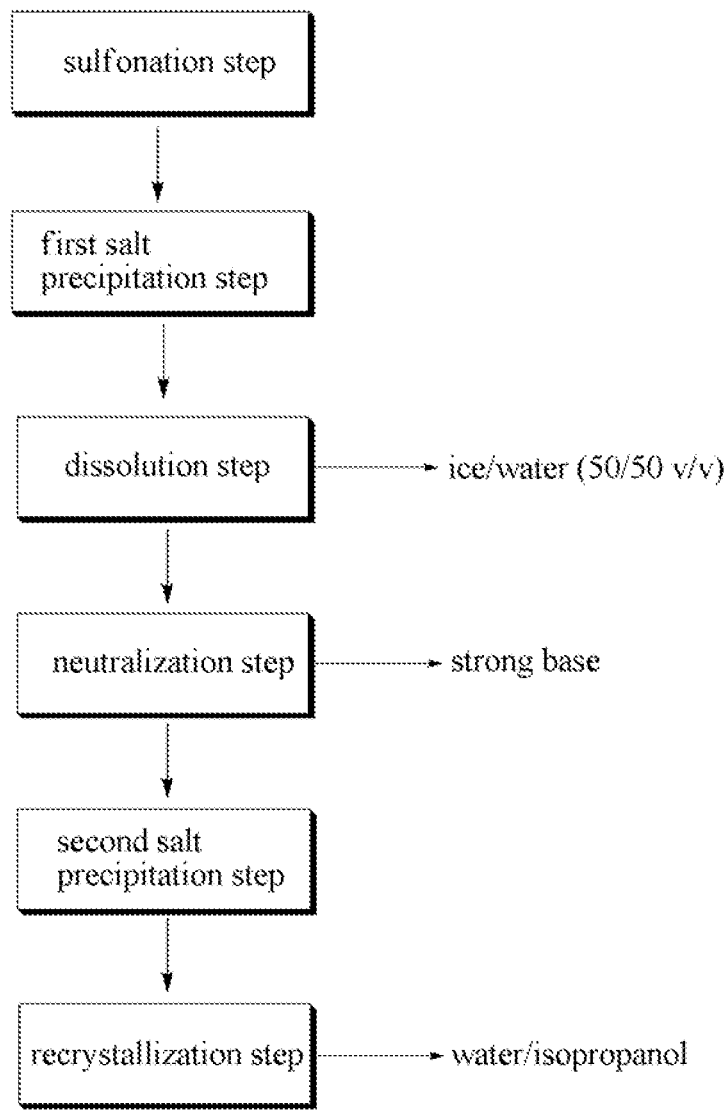
FIG. 1 is a flowchart showing a conventional process for purifying a sulfonated aromatic monomer.
Figure 2:
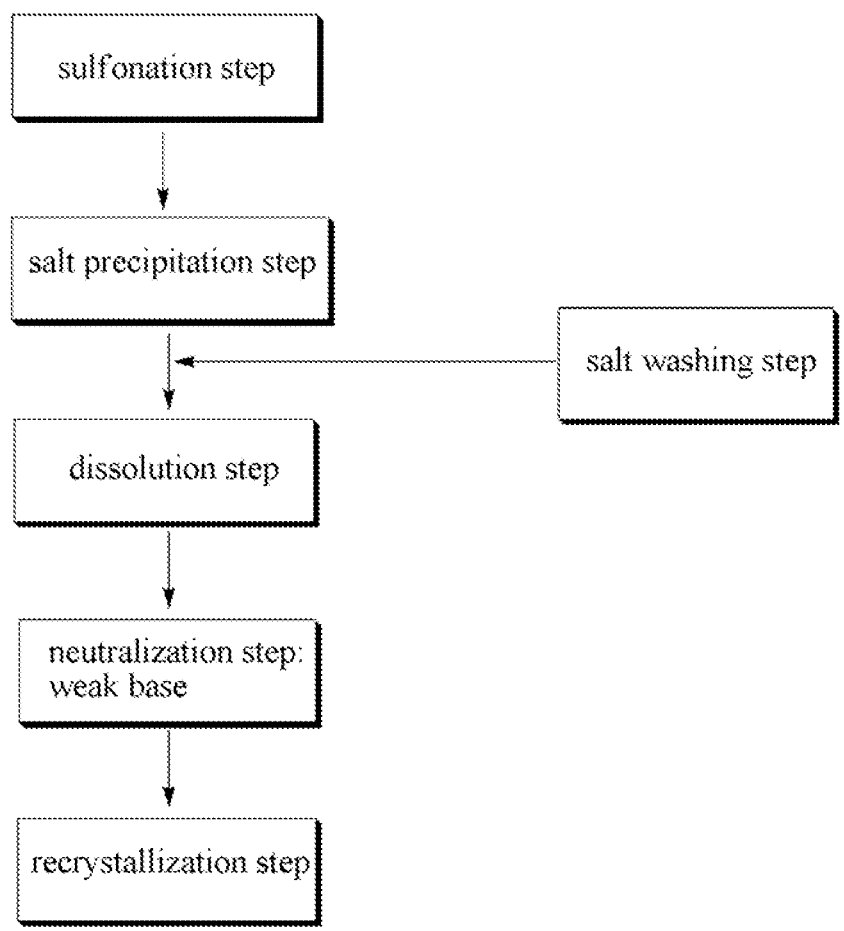
FIG. 2 is a flowchart showing a process for purifying a sulfonated aromatic monomer according to a first preferred embodiment of the present invention.

FIG. 2 is a flowchart showing a process for purifying a sulfonated aromatic monomer according to a first preferred embodiment of the present invention, and FIG. 3 is a flowchart showing a process for purifying a sulfonated aromatic monomer according to a second preferred embodiment of the present invention. As shown therein, in the method for purifying the sulfonated aromatic monomer according to the present invention, while the reaction conditions used in the conventional method for purifying the sulfonated aromatic monomer are maintained, the number of the salt precipitation steps is reduced, the recrystallization step is simplified, and the purification step is carried out using an easily available, stable substance under economical and mild conditions.

FIG. 4 shows the 1H NMR spectrum of the sulfonated aromatic monomer obtained by the purification method of the present invention. As can be seen therein, the sulfonated aromatic monomer was synthesized with high purity.

Further, the sulfonated aromatic monomer purified by the purification method of the present invention can be used for the preparation of a polymer for a polymer electrolyte membrane, and the polymer has an intrinsic viscosity of 1.0-3.0 dl/g, suggesting that the sulfonated aromatic monomer will be advantageous to synthesize polymer with high molecular weight.

MODE FOR INVENTION

Hereinafter, the present invention will be described in further detail with reference to examples. It is to be understood, however, that these examples are for illustrative purposes only and are not intended to limit the scope of the present invention.

Example 1

Prepare of Pure Disulfonated Dichlorodiphenyl Sulfone (SDCDPS)

In a 3-neck flask, 28.7 g (99 mmol) of 4,4'-dichlorodiphenyl sulfone (DCDPS) was dissolved in 35 ml of 65% fuming sulfuric acid. The solution was completely dissolved by heating at 110° for 6 hours. Then, the solution was cooled to room temperature and poured onto 400 ml of ice, and 180 g of sodium chloride (NaCl) was added thereto to precipitate a disulfonated dichlorodiphenyl sulfone (SDCDPS) salt substituted with sodium ion. The precipitate was filtered under reduced pressure, and the resulting salt was washed 1-3 times with 50 ml of ethanol to remove the remaining sulfuric acid. The material resulting from the ethanol washing process was dissolved in 100 ml of distilled water, and an aqueous solution of 2N $Na_2CO_3$ was slowly added dropwise thereto to adjust the pH to 6-7. Then, the resulting aqueous solution was distilled under reduced pressure to remove a slight amount of water and allowed to stand in a cold place (refrigerator) for about one day, thereby obtaining a white pure crystal. The obtained crystal was dried in a vacuum oven at 100° for about 2 days, thereby obtaining pure disulfonated dichlorodiphenyl sulfone (SDCDPS).

Example 2

Preparation of Pure Disulfonated Dichlorodiphenyl Sulfone

In a 3-neck flask, 28.7 g (99 mmol) of 4,4'-dichlorodiphenyl sulfone (DCDPS) was dissolved in 0.35 ml of 65% fuming sulfuric acid. The solution was completely dissolved by heating at 110° C. for 6 hours. Then, the solution was cooled to room temperature and poured onto 400 ml of ice, and 180 g of sodium chloride (NaCl) was added thereto to precipitate a disulfonated dichlorodiphenyl sulfone (SDCDPS) salt substituted with sodium ion. The precipitate was filtered under reduced pressure, and the resulting salt was washed 1-3 times with 50 ml of ethanol to remove the remaining sulfuric acid. The material resulting from the ethanol washing process was dissolved in 100 ml of distilled water, and then passed through 50 g of an anion exchange resin comprised of $NH_3^+Cl^-$ coupled to a polystyrene structure in a filter funnel. The SDCDPS received in an Erlenmeyer flask was passed again through the anion exchange resin, and this process of passing the SDCDPS through the anion exchange resin was repeated 1-3 times. Then, the disulfonated dichlorodiphenyl sulfone (SDCDPS) attached to the anion exchange resin was detached using the same amount of a base as that of the anion exchange resin. The resulting solution was distilled under reduced pressure to remove water, and then allowed to stand in a cold place (refrigerator) for one day, thereby obtaining a white pure crystal. The obtained crystal was dried in a vacuum oven at 100° C. for about 2 days, thereby obtaining pure disulfonated dichlorodiphenyl sulfone (SDCDPS).

Comparative Example 1

Preparation of Disulfonated Dichlorodiphenyl Sulfone

In a 3-neck flask, 28.7 g (99 mmol) of 4,4'-dichlorodiphenyl sulfone (DCDPS) was dissolved in 60 ml of 30% fuming sulfuric acid (more than 3 equivalents). The solution was completely dissolved by heating at 110° C. for 6 hours. Then, the solution was cooled to room temperature and poured added to 400 ml of ice water, and 180 g of sodium chloride (NaCl) was added thereto to precipitate a disulfonated dichlorodiphenyl sulfone (SDCDPS) salt substituted with sodium ion. The precipitate was filtered under reduced pressure, and the filtrate was dissolved in 400 ml of distilled water and then adjusted to a pH of 6-7 by adding 2N NaOH thereto in small amounts.

After the neutralization step, 180 g of sodium chloride (NaCl) was added to the solution to precipitate a disulfonated dichlorodiphenyl sulfone (SDCDPS) salt again. The precipitated material was filtered under reduced pressure and recrystallized from a 5:5 mixture of isopropanol and water. The resulting material was allowed to stand in a cold place for about one day, thereby obtaining a needle-like white crystal. The crystal was dried in a vacuum oven at 100° for about 2 days.

Test Example 1

The disulfonated dichlorodiphenyl sulfone (SDCDPS), prepared and purified in each of Examples 1 and 2, was analyzed by an NMR spectrophotometer (Bruker AMX-300 MHz).

As a result, as can be seen in the $^1$H NMR spectrum in FIG. 4, the disulfonated dichlorodiphenyl sulfone compound was synthesized with high purity.

Test Example 2

The kind and content of element in the disulfonated dichlorodiphenyl sulfone (SDCDPS), prepared and purified in each of Examples 1 and 2, were analyzed by an ICP (inductively coupled plasma-atomic emission) analyzer. Table 1 below shows the results of analyzing the content of sodium (Na) element in the compound obtained in each of Examples 1 and 2. As can be seen therein, the measured content of sodium was similar to the theoretical value, suggesting that the disulfonated dichlorodiphenyl sulfone as the target compound was synthesized with high purity.

TABLE 1

Results of analysis of sodium content

| | Theoretical value (%) | Measured value (%) |
|---|---|---|
| Example 1 | 9.35 | 9.25 |
| Example 2 | 9.35 | 9.30 |

INDUSTRIAL APPLICABILITY

As described above, the present invention provides an improved method for purifying a sulfonated aromatic monomer. Specifically, the improved purification method of the present invention is an economical method capable of providing a highly pure sulfonated aromatic monomer, in which the salt precipitation step and the recrystallization step are simplified while maintaining the reaction conditions used in the conventional method for synthesizing the sulfonated aromatic monomer, and the purification process is carried out using an easily available and safe-to-handle chemical substance.

Further, the sulfonated aromatic monomer purified by the purification method of the present invention will be useful for the preparation of a polymer for a polymer electrolyte membrane. When a polymer is synthesized using the sulfonated aromatic monomer purified by the purification method of the present invention, the polymer has an intrinsic viscosity of 1.0-3.0 dl/g, suggesting that the sulfonated aromatic monomer will be advantageous to synthesize polymer with high molecular weight.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for purifying a sulfonated aromatic monomer represented by formula 1 as shown in the following reaction scheme 2, the method comprising the steps of:

allowing an aromatic monomer 3 to react with fuming sulfuric acid 4 to prepare a sulfonated aromatic compound 2;
adding a salt to the compound 2 to precipitate a crude compound 1-1;
dissolving the crude compound 1-1 in water, wherein the step of dissolving the crude compound is carried out after washing the crude compound with alcohol selected from among methanol, ethanol or a mixture thereof to remove sulfuric acid remaining in the crude compound 1-1;
neutralizing the aqueous solution containing the crude compound, wherein the step of neutralizing the aqueous solution containing the crude compound is carried out using any one weak base selected from the group consisting of sodium carbonate, sodium hydrogen carbonate, ammonium hydroxide, ammonia, sodium phosphate and sodium sulfate; and
concentrating the neutralized aqueous solution and recrystallizing the concentrate from water, wherein alcohol is not added during the steps of neutralizing and recrystallizing:

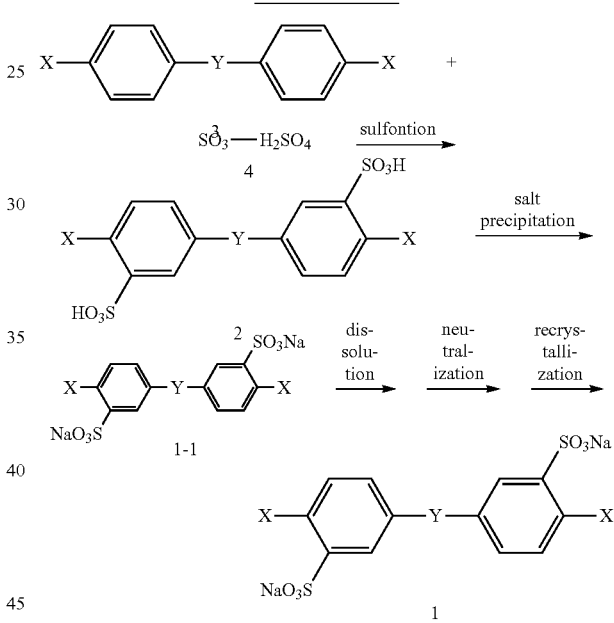

Reaction Scheme 2 wherein X is a halogen group element, and Y is any one selected from the group consisting of —S—, —C=O—, —P(O)(C$_6$H$_5$)— and —SO$_2$—.

2. A method for a sulfonated aromatic monomer represented by formula 1 as shown in the following reaction scheme 2, the method comprising the steps of:

allowing an aromatic monomer 3 to react with fuming sulfuric acid 4 to prepare a sulfonated aromatic compound 2;
adding a salt to the compound 2 to precipitate a crude compound 1-1;
dissolving the crude compound 1-1 in water;
neutralizing the aqueous solution containing the crude compound, wherein the step of neutralizing the aqueous solution containing the crude compound is carried out by neutralizing the aqueous solution with anion exchange resin, followed by a washing step; and
concentrating the neutralized aqueous solution and recrystallizing the concentrate from water, wherein alcohol is not added during the steps of neutralizing and recrystallizing:

Reaction Scheme 2
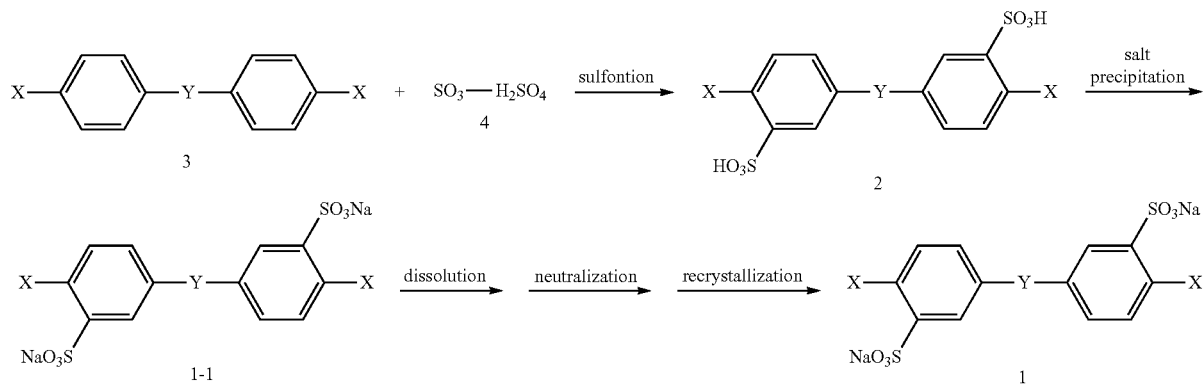
wherein X is a halogen group element, and Y is any one selected from the group consisting of —S—, —C=O—, —P(O)(C$_6$H$_5$)— and —SO$_2$—.
3. The method of claim 2, wherein the washing step is carried out by washing the anion exchange resin with the same amount of a base as that of the anion exchange resin.
* * * * *